(12) United States Patent
Brasier et al.

(10) Patent No.: US 8,053,199 B2
(45) Date of Patent: Nov. 8, 2011

(54) MOLECULAR PHENOTYPING OF SEVERE ASTHMA

(76) Inventors: Allan R. Brasier, Galveston, TX (US); William J. Calhoun, League City, TX (US); Gary D. Boetticher, Houston, TX (US)

( * ) Notice: Subject to any disclaimer, the term of this patent is extended or adjusted under 35 U.S.C. 154(b) by 292 days.

(21) Appl. No.: 12/220,263

(22) Filed: Jul. 22, 2008

(65) Prior Publication Data

US 2009/0068689 A1 Mar. 12, 2009

Related U.S. Application Data

(60) Provisional application No. 60/961,631, filed on Jul. 23, 2007.

(51) Int. Cl.
*G01N 33/53* (2006.01)

(52) U.S. Cl. .............................. 435/7.1; 435/4

(58) Field of Classification Search .................. None
See application file for complete search history.

(56) References Cited

OTHER PUBLICATIONS

Bullens et al (2006), Respiratory Research, 7:135.*
Bhattacharjee, et al. Classification of Human Lung Carcinomas by mRNA Expression Profiling Reveals Distinct: *Proc National Academy Science*, Nov. 20, 2001, vol. 98, No. 24, pp. 13790-13795.
Deykin A. et al. Biomarker-driven Care in Asthma: Are we there? *Journal of Allergy and Clinical Immunology*, Sep. 2006, vol. 118, No. 3, pp,. 565-568.
Golub, T.R. et al. Molecular Classification of Cancer: Class Discovery and Class Prediction by Gene Expression Monitoring: *Science*, Oct. 15, 1999, vol. 286, No. 5439, pp. 531-537.
Godard P., et al. Costs of Asthma are Correlated with Severity a 1-yr Prospective Study: *European Respiratory Journal*, 2002, vol. 19, pp. 61-67.
Holgate, S.T. et al. Release of RANTES, MIP-1 $\infty$, and MCP-1 into Asthmatic Airways Following Endobronchial Allergen Challenge: *American Journal of Respiratory and Critical Care Medicine*, 1997, vol. 156, pp. 1377-1383.
Jatakanon, A. et al. Neutrophilic Inflammation in Sever Persistent Asthma; *American Journal of Respiratory and Critical Care Medicine*, 1999, vol. 160, No. 1532-1539.
Kapp, A.V. et al. Discovery and Validation of Breast Cancer Subtypes; *BioMed Central Genomics*, 2006, vol. 7, No. 1, p. 231.
Moore et al. Characterization of the Sever Asthma Phenotype by the National Heart, Lung, and Bloog Institute's Severe Asthma Research Program; *Journal of Allergy and Clinical Immunology*, 2007, vol. 119, No. 2, pp. 405-413.
Moore, et al. Sever Asthma: An overview; *Journal of Allergy and Clinical Immunology*, Mar. 2006, vol. 117, pp. 487-494.
Quinlan, et al. C4.5: Programs for Machine Learning: *Machine Learning*, 1994, vol. 16, pp. 235-240.
Serra-Battles, et al. Costs of Asthma According to the Degree of Severity: *European Respiratory Journal*, 1998, vol. 12, pp. 1322-1326.
Tomas, MS et al. Regulation of Cockroach Antigen-Induced Allergic Airway Hyperreactivity by the CXCR3 Ligand CXCL9 [1]:*The Journal of Immunology*, 2004, vol. 173, pp. 615-623.
Wenzel, SE et al. Evidence that Severe Asthma Can be Divided Pathologically into two Inflammatory Subtypes with Distinct Physiologic and Clinical Characteristics; *America Journal of Respiratory and Critical Care Medicine*, 1999, vol. 160, No. 3, pp. 1001-1008.
Wenzel, et al. Severe asthma: Lessons from the Severe Asthma Research Program: *Journal of Allergy and Clinical Immunology*, 2007, vol. 119, No. 1, pp. 14-21.

* cited by examiner

*Primary Examiner* — Prema Mertz
(74) *Attorney, Agent, or Firm* — Benjamin Aaron Adler

(57) ABSTRACT

The present invention discloses a method for classifying individuals into those who have airway hyperreactvitiy and those with asthma based on cytokine expression patterns. It is contemplated that such a method will enable rapid identification of individuals requiring intensive treatment for asthma, thereby reducing morbidity and improving quality of life for those affected.

4 Claims, 8 Drawing Sheets

MOLECULAR PHENOTYPING OF SEVERE ASTHMA

CROSS REFERENCE TO RELATED APPLICATION

This non-provisional application claims benefit of provisional application U.S. Ser. No. 60/961,631 filed on Jul. 23, 2007, now abandoned.

FEDERAL FUNDING LEGEND

This invention was produced in part using funds obtained through National Institute of Allergy and Infectious Diseases grant AI062885, National Heart, Lung and Blood Institute award BAA-HL-0204 and National Institute of Environmental Health Sciences award P30 ES06676. Consequently, the federal government has certain rights in this invention.

BACKGROUND OF THE INVENTION

1. Field of the Invention

The present invention relates generally to the fields of immunology and molecular biology. Specifically, the present invention identifies molecular classifiers of hyperreactivity, which will allow rapid identification of individuals with asthma. This rapid identification will help clinical investigation on the etiology and intervention for asthma.

2. Description of the Related Art

Asthma is a chronic inflammatory disease of the airways characterized by recurrent episodes of symptomical airflow obstruction and various degrees of airways hyperreactivity to nonspecific stimuli (Busse and Lemanske, 2001). The recognition that this disease has a chronic inflammatory component has directed therapy towards early use of inhaled glucocorticoid therapy, typically producing significant reductions in inflammatory markers, and improvement in pulmonary function (Busse and Lemanske, 2001). However, there is a subset of patients (~5-7%) with "severe", or "refractory" asthma that do not respond to glucocorticoids. These patients account for 40-50% of the health costs of asthma, and incur significant morbidity and decrements in quality of life (Godard et al., 2002; Serra-Battles, 1998).

Severe asthma is a heterogeneous disorder with distinct ages of onset, duration of disease, degree of airflow impairment, presence of modifying factors (GERD, sinusitis), and type of underlying inflammation (Moore and Peters, 2006; Wenzel et al., 1999). In this regard, phenotypic analysis of severe asthmatics prospectively enrolled in the Severe Asthma Research Program (SARP) has shown that severe asthmatics tend to be older and have a greater frequency of respiratory infection (sinusitis and/or pneumonia), suggesting that as a group, they have alterations in innate immune defenses (Moore et al., 2007). Additionally, at least some severe asthmatics have been characterized as having either neutrophil-predominant inflammation, or increased tissue eosinophils by endobronchial biopsy (Wenzel, 2003; Jatakanon et al., 1999). These latter patients have been shown to increase near-fatal events, especially those with early onset disease, and are associated chronic airway remodeling, indicated by increased sub-basement membrane thickening (Wenzel et al., 1999). However, others have found no clinical differences between the eosinophilic and noneosinophilic phenotypes (Lemiere et al., 2006). Together, these observations suggest that severe asthma is a pathologically heterogenous disorder that still lacks an objective method for distinguishing clinically significant subtypes.

Thus, prior art in diagnostic assays that will allow medical personnel to rapidly identify individuals who may benefit from more intensive treatment of their asthma, thereby reducing morbidity and improving quality of life for those affected. The present invention full fills this long-standing need and desire in the art.

SUMMARY OF THE INVENTION

Severe asthmatics have distinct inflammatory processes suggesting that they may also express distinct airway cytokine profiles compared to those with responsive asthma. The present invention examined the airway cytokine expression patterns in bronchoalveolar lavage (BAL) from a matched group of non-severe and severe asthmatics using bead-based multiplex cytokine arrays (luminex xMAP). The data were analyzed using both unsupervised and supervised classification methods to identify informative cytokine patterns for subtypes of asthma and predictors of methacholine hyperresponsiveness. Accurate definition of asthmatic phenotypes based on molecular profiles may facilitate clinical investigation on the etiology, pathogenesis and intervention for asthma.

The present invention is directed to a method of detecting asthma in an individual. Such a method comprises obtaining a biological sample from the individual. The expression of cytokines comprising IL-1Rα, MIP-1α, MIG, IL-15, IL-2R, IL-10, IL-4, IL-6, MCP-1, IL-2 or a combination thereof at the protein level is then examined in such a sample. This is followed by a statistical analysis on the expression levels of the cytokines in the individual compared to those in normal individual, where reduced levels, increased levels or a combination thereof of the cytokine in the sample of the individual compared to the expression levels in the sample of the normal individual indicates that the individual has asthma.

The present invention is also directed to a method of detecting airway hyperreactivity in an individual. Such a method comprises obtaining a biological sample from the individual. The expression of cytokines comprising IL-2, IL-4, IL5, TNFα, MIG, RANTES or a combination thereof at the protein level is then examined in such a sample. This is followed by a statistical analysis on the expression levels of the cytokines in the individual compared to those in normal individual, where reduced levels, increased levels or a combination thereof of the cytokine in the sample of the individual compared to the expression levels in the sample of the normal individual indicates that the individual has airway hyperreactivity.

The present invention is further directed to a method of differentiating airway hyperreactivity and asthma in an individual. Such a method comprises obtaining a biological sample from the individual. The expression of cytokines comprising IL-1Rα, MIP-1α, MIG, IL-15, IL-2R, IL-10, IL-4, IL-6, MCP-1, IL-2, IL-5, TNFα, RANTES or a combination thereof at the protein level is examined in the sample. This is followed by performing statistical analysis on the expression levels of the cytokines in the individual compared to those in normal individual, where reduced levels, increased levels or a combination thereof of the cytokine in the sample of the individual compared to the expression levels in the sample of the normal individual indicates that the individual has airway hyperreactivity or asthma.

Other and further aspects, features and advantages of the present invention will be apparent from the following description of the embodiments of the invention given for the purpose of the disclosure."

BRIEF DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIG. 6A: BAL eosinophils; FIG. 6B: PC20 methacholine.

FIG. 7A: Frequency for total BAL eosinophil count (in millions) in the study population. The population cut-off for "high eosinophils" is indicated. FIG. 7B: Frequency of neutrophil count (in millions). FIG. 7C: Bronchodilators in response to β-agonist. Plotted on the x axis is percent change $FEV_1$ in response to albuterol inhalation. FIG. 7D: Methacholine hyper-responders. X axis is $PC_{20}$ methacholine. The cut-offs used to define eosinophil rich, neutrophil rich, bronchodilator response and methacholine hyper-sensitive classes are shown.

FIG. 8A: ROC of high eosinophil model. In these plots, the x axis is 1-specificity and y axis is sensitivity. FIG. 8B: ROC of high neutrophil model. FIG. 8C: ROC of bronchodilator model. FIG. 8D: ROC of methacholine hyper-responder model.

DETAILED DESCRIPTION OF THE INVENTION

Figure 1:
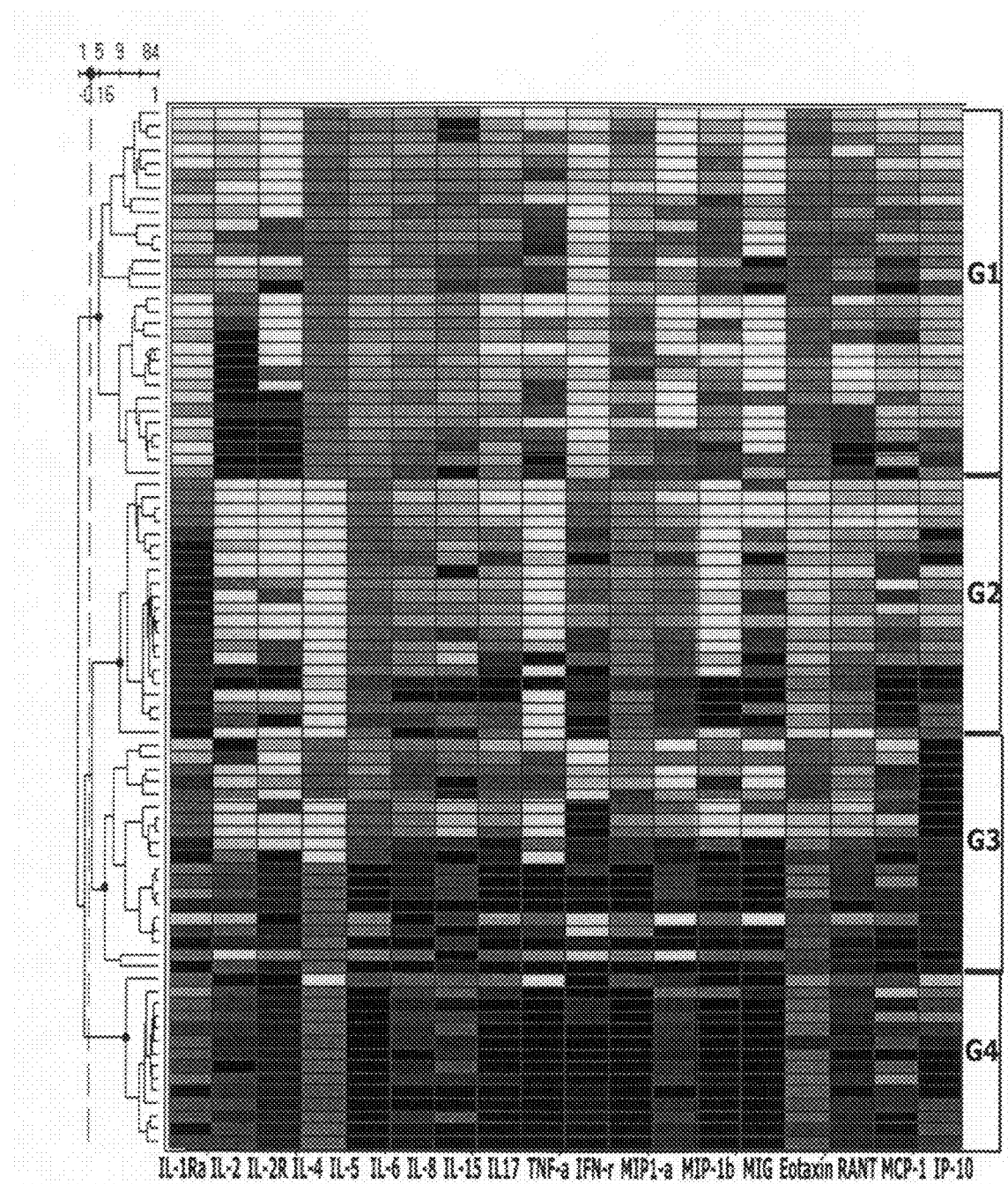
FIG. 1 shows hierarchical clustering of 18 cytokines. This figure shows a heat map of clustering cytokine values. Each row is an individual patient. At left, is a dendogram showing similarity of groups. At right, four major groups (G) are indicated by vertical bars.
Figure 2:
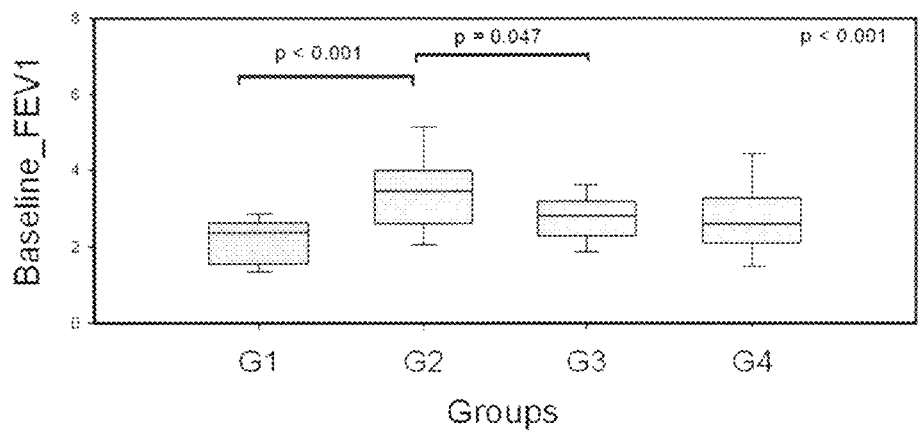
FIG. 2 shows pair-wise comparison of the four asthmatic groups using multiple comparison (bonferroni correction). Shown herein is a box plot for baseline $FEV_1$. For each pair-wise comparison, the p value between the groups is indicated.
Figure 3:
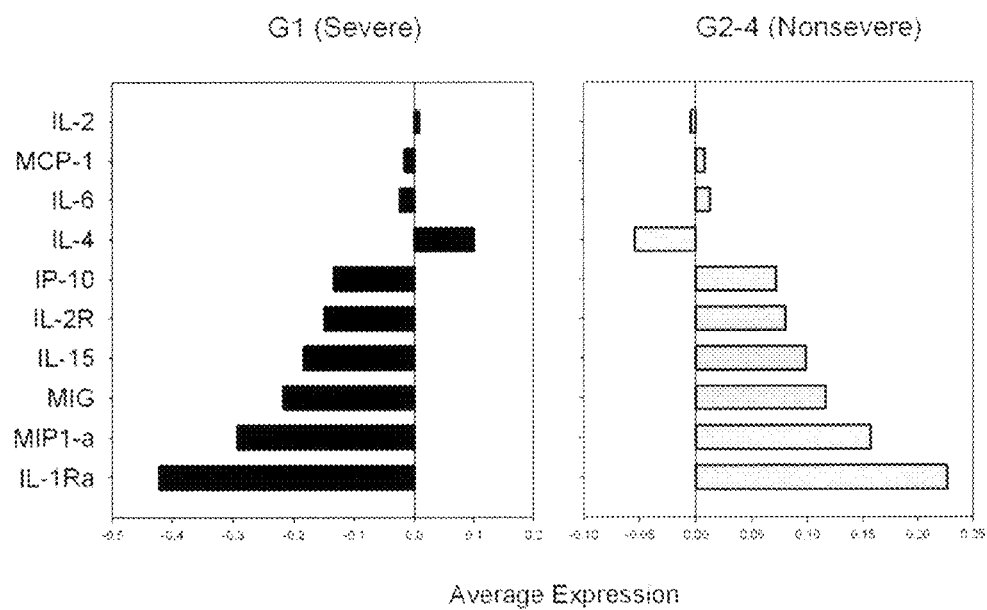
FIG. 3 shows shrunken centroid classifiers for G1. Shown herein is a rank-ordered list of the 10 cytokines that minimize cross validation error for G1 asthmatics. On the left, is the centroid of G1 and on the right, is the centroid of combined G2-G4 (threshold of 1.2). X axis, is deviation from the overall class centroid.

A current major challenge in the management of asthma is to accurately identify subtypes that differ in disease pathogenesis and response to therapy. Severe asthma is differentiated from mild-moderate disease by age of onset, duration of disease, degree of airflow impairment, cellular inflammation, presence of sinusitis and history pneumonia (Moore and Peters, 2006; Moore et al., 2007). However, these clinical features as well as noninvasive measurements of airway inflammation (sputum eosinophils and exhaled NO) have not resulted in a method for unambiguous separation of clinical phenotype, response to therapy or disease course (Moore and Peters, 2006; Deykin, 2006).

The approach of the present invention was based on identifying subgroups of asthma based on a biologically objective marker (BAL cytokine concentration), and using data mining techniques to group subjects independently of any bias based on clinical assessment. This approach has the potential to accurately identify distinct groups of asthmatics based on commonalities in disease mechanisms. For example, similar approaches have used mRNA expression patterns different groups of responsive and unresponsive cancers. Using mRNA profiles, subjects can be identified using that are otherwise indistinguishable using conventional clinical staging criteria (Tibshirani et al., 2002; Golub et al., 1999; Bhattacharjee et al., 2001; Kapp et al., 2006). However, whether this method for molecular phenotyping is generally applicable to other diseases, including asthma, has not been addressed.

The present invention is based on finding characteristic patterns of cytokines present in the airway lining fluids of patients with airway hyper-reactivity. The present invention determined that a method for interpreting a group of 10 cytokines is highly accurate for predicting who has airway hyper-reactivity and who has severe asthma. Based on expression values of 10 cytokines in BAL, the unsupervised analysis discussed herein indicates that at least four phenotypically distinct subgroups of asthma can be identified. Of interest, G1 represents a group enriched in subjects that meet the ATS consensus definition for severe asthma. This group is characterized by increased BMI, reduced $FEV_1$, reduced FVC, and enhanced sensitivity to methacholine.

Importantly, findings of the present invention indicate that no single cytokine value can be used to separate subjects into these groups, but rather, an expression pattern consisting of a minimum of 10 distinct cytokines must be considered. Relative to the others in this study, the G1 grouping is characterized by reduced levels of IL-1Ra, MIP-1a, MIG and others which are known to play various important roles in coordinating cellular trafficking and inflammation in the airways. For example, IL-1Ra is expressed at increased levels in asthmatic epithelium (Sousa et al., 1997), where its actions are to block IL-1a/b mediated inflammation by competition for receptor binding. The reduction in IL-1Ra may result in enhanced IL-1 signaling, resulting in neutrophilic inflammation, a feature characteristic of severe asthma (Jatakanon et al., 1999). Similarly MIP-1a is a CC chemokine expressed by macrophages and airway epithelial cells to induce chemotaxis of CD8 T-lymphocytes and eosinophils. The secretion of MIP-1 is inhibited by glucocorticoids, and subjects with severe asthma are on greater doses of steroid therapy (Holgate et al., 1997). The IFN-g inducible MIG(CXCL9) significantly reduces airway hyperresponsiveness and eosinophil accumulation in animal models of allergen challenge (Thomas et al., 2004). MIG diminishes IL-4 and enhances IL-12 levels, directing activated T cells toward a $T_H1$ phenotype. The reduction in these cytokines in the G1 group relative to the less severe asthmatics therefore, are biologically plausible with the understanding of the pathogenesis of severe asthma.

Currently, most molecular classifiers that have been produced are based on mRNA expression patterns. However, it is suggested that protein expression profiles may be more useful markers of disease than gene expression patterns. This may be particularly true when the proteins themselves play important roles in the underlying disease process, such as cytokines in asthma, and therefore represent bona fide biomarkers. Although previous work of examining expression of selected cytokines have shown some associations with asthma severity, these associations are not strong and have not been widely replicated. For example, IL-8 was shown to be enhanced in severe asthmatics during an acute exacerbation and correlates with the number of neutrophils (Fahy et al., 1995). This study was conducted on stable asthmatics, and the processes involved in chronic inflammatory state may be different from those producing acute exacerbations. Other studies have shown increased IL-2 and IL-4 levels in severe asthmatics (Leung and Szefler, 1997), where increased IL-2 and IL-4 mRNA has been observed in BAL cells (Leung et al., 1995). Although no difference was demonstrated in BAL concentrations for IL-2 or -4 between severe and nonsevere asthmatics in the data set herein, these cytokines do contribute to a model predicting methacholine HR.

The classification tree analysis discussed herein has yielded two important findings. First, methacholine HR can be accurately separated from LR based on cytokine profiles in bronchoalveolar lavage, and second, that the group of methacholine HR consists of at least three phenotypically distinct classes. Intriguingly, although increased IL-2 and IL-4 have been reported in severe asthmatics, HR Class A is characterized by low levels of all three cytokines, and is a class containing those subjects with the lowest $PC_{20}$ methacholine responses in the present invention. It is contemplated to extend this analysis to larger independent data sets to determine whether the subjects in the HR Classes have distinct clinical outcomes.

The feature reduction analysis has shown that at least 5 cytokines can be used to separate HR from LR in this dataset. It is also important to note that there are important differences in the groups of cytokines that identify G1 with those that identify HR. Specifically, IL-5, secreted into the bronchoalveolar lavage in response to allergen challenge, and a molecule important in eosinophil recruitment and survival, was identified as an important classification variable in HR, but not for G1. This observation may explain why single cytokine values alone may not be useful discriminators in asthma. Further exploration of these data are underway.

The present invention provides a first proof of concept that informative patterns of cytokines can be detected and interpreted in bronchoalveolar lavage from patients with asthma and may contribute to more objective classification of disease type. It is contemplated herein that such a method will allow the treating physician to more rapidly identify who may benefit from more intensive treatment of their asthma, reducing morbidity and improving the quality of life for those affected. Moreover, these findings can be interpreted to suggest that subjects with apparently similar clinical characteristics are in fact, composed of heterogeneous subtypes that can be further distinguished based on bronchoalveolar lavage cytokine profiles.

In one embodiment of the present invention there is provided a method of detecting asthma in an individual, comprising obtaining a biological sample from the individual; examining the expression of cytokines comprising IL-1Rα, MIP-1α, MIG, IL-15, IL-2R, IL-10, IL-4, IL-6, MCP-1, IL-2 or a combination thereof at the protein level in the sample; and performing statistical analysis on the expression levels of the cytokines in the individual compared to those in normal individual, where reduced levels, increased levels or a combination thereof of the cytokine in the sample of the individual compared to the expression levels in the sample of the normal individual indicates that the individual has asthma. This method may further comprise classifying the asthama into severe and not severe subtypes. Such a classification is based on the expression profile of the cytokine made using a computerized program.

Additionally, the expression of the cytokine at the protein level may be measured by ELISA. Further, the statistical analysis performed in such a method may be hierarchical cluster analysis. Examples of the cytokine with reduced expression level may include but is not limited to IL-1Rα, MIP-1α, MIG, IL-15, IL-2R, IL-10, IL-6, MCP-1 or a combination thereof and those with increased expression level may include but is not limited to IL-4, IL-2 or both. Furthermore, the biological sample used in such a method may include but is not limited to sputum, respiratory fluid or serum. Examples of the individual benefitting from such a method may include but is not limited to an individual at risk or suspected of suffering from asthma or previously diagnosed with asthma.

In another embodiment of the present invention there is provided a method of detecting airway hyperreactivity in an individual, comprising: obtaining a biological sample from the individual; examining the expression of cytokines comprising IL-2, IL-4, IL-5, TNFa, MIG, RANTES or a combination thereof at the protein level in the sample; and performing statistical analysis on the expression levels of the cytokines as compared to those in normal individuals. In this process, a series of decisions based on the relative level of these cytokines in the sample of the individual compared to the expression level in the sample of a normal individual indicates that the individual has one of several types of airway hyperreactivity. For example, one class of hyperreactivity is characterized by high IL-2 levels. A second class has low IL-2 levels, low IL-5 levels and low IL-4 levels. Another class has low IL-2 levels and high IL-5 levels. Similar decisions can be made by considering the patterns of the TNF, MIG and RANTES cytokines. This method may further comprise classifying the individual into one of at least three classes of hyper-responders and low responders. Such a classification is based on the expression profiles of the cytokines.

Additionally, the expression of the cytokine at the protein level may be measured by ELISA or multiplex bead based assays. Further, the statistical analysis is a decision tree analysis using various combinations of IL-2, IL-4, IL-5, TNFa, MIG, RANTES concentrations as described above. The biological sample used in such a method may include but is not limited to sputum, respiratory fluid or serum. Further, the individual benefiting from such a method may include but is not limited to an individual at risk or suspected of suffering from airway hyperreactivity or previously diagnosed with airway hyperreactivity.

In yet another embodiment of the present invention there is provided a method of differentiating subtypes of asthma in an individual, comprising: obtaining a biological sample from the individual; examining the expression of cytokines comprising IL-1Ra, MIP-1a, MIG, IL-15, IL-2R, IL-10, IL-4, IL-6, MCP-1, IL-2, IL-5, TNFa, RANTES or a combination thereof at the protein level in the sample; and performing statistical analysis on the expression levels of the cytokines in the individual compared to reference asthmatics. This analysis involves hierarchical clustering where the reduced levels, increased levels or a combination thereof of the cytokine in the sample of the individual compared to the expression levels in the sample of the reference indicates that the individual has a particular subtype of asthma. An individual with asthma as determined by such a method may have reduced levels of IL-1Ra, MIP-1a, MIG, IL-15, IL-2R, IP-10, IL-6, MCP-1 and increased IL-4 and IL2. Such an individual may further be classified into a subgroup of asthma.

In yet another embodiment of the present invention the classification of either subgroup of airway hyperreactivity or subgroup of asthma based on the measurement of cytokine (by ELISA or multiplex cytokine assay) combined with statistical analysis (decision tree or hierarchical clustering or related machine learning tool) is used to select the type and duration of anti-asthma treatment. For example, an individual with Group 1 asthma may be given a different combination of glucocorticoids, anti-cholinergic agents or leukotriene modifiers than an individual with Group 2 asthma.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Subjects

In the Severe Asthma Research Program, enrollees are categorized as 1) healthy volunteer, 2) non-severe asthma, and 3) severe asthma, on the basis of a standardized manual of procedures (MOP) based on an NHLBI workshop (Wenzel and Busse, 2007, Proceedings of the ATS workshop on Refractory Asthma, 2000). All enrollees have history, physical examination, spirometry, bronchodilator reversibility, allergy skin testing, and methacholine challenge testing. Healthy volunteers have normal lung function and negative methacholine challenge, no history of asthma, negative skin tests to common aeroallergens, and no need for any routine medications. Non-severe asthmatics have lung function that can be normalized using standard doses of inhaled corticosteroids, with or without long-acting beta-agonists or leukotriene modifiers; in addition, they must have at least 2 positive allergy skin tests. Severe asthmatics are defined according to ATS consensus for refractory asthma (Wenzel and Busse, 2007). These subjects are characterized by abnormal lung function in the face of aggressive standard inhaled steroid therapy and at least one additional control agent; they must in addition have at least 2 positive skin tests. Subjects performed spirometry before and after up to 8 puffs (90 µg/puff) of albuterol. The baseline FEV1 testing required a 4-6 hr withhold of short acting bronchodilators and a 10-12 hr hold for long acting bronchodilators. Hankonsen predicted values (with race correction) were utilized to obtain "percent predicted" values. Studies were approved by the local institutional review boards and subjects gave informed consent.

EXAMPLE 2

Bronchoalveolar Lavage

Bronchoscopy and bronchoalveolar lavage were conducted according to the Severe Asthma Research Program manual of procedures. Briefly, after topical anesthesia, bronchoscopy was performed. Bronchoalveolar lavage was obtained using 2 aliquots of 50 ml each of 0.9% NaCl. Cells were separated by low speed centrifugation (400×g, 20 min), and supernatants frozen for subsequent analysis. Bronchoalveolar lavage and de-identified clinical information were obtained from the SARP for 84 randomly selected subjects matched for age and gender (Table I); by the SARP criteria, 43 were "non-severe" and 41 were "severe" asthmatics.

TABLE I

| Phenotype | Characteristic | Men 30 (36%) | Women 54 (64%) | All Subjects |
|---|---|---|---|---|
| Not Severe (n = 43) | | 15 (34.9%) | 28 (65.1%) | 43 (100%) |
| | Age of onset | 11.6 ± 10.4 | 18.6 ± 11.5 | 16 ± 11.5 |
| | Baseline $FEV_1$ (I) | 3.7 ± 1 | 2.8 ± 0.6 | 3.14 ± 1$^§$ |
| | Baseline $FEV_1$ (% pred.) | 85.4 ± 18.1 | 90.2 ± 16.2 | 88.5 ± 16.8$^§$ |
| | Baseline FVC (I) | 5.3 ± 0.9 | 3.6 ± 0.7 | 4.2 ± 1.15$^§$ |
| | Baseline FVC (% pred.) | 97.7 ± 12.3 | 99.2 ± 15.7 | 98.6 ± 4.5$^§$ |
| | MaxFEV1 Reversal | 10.1 ± 5.8 | 12.3 ± 11.4 | 11.5 ± 9.8* |
| Severe (n = 41) | | 15 (36.6%) | 26 (63.4%) | 41 (100%) |
| | Age of onset | 10.2 ± 12.3 | 16.4 ± 15.4 | 14.1 ± 14.6 |
| | Baseline $FEV_1$ (I) | 2.3 ± 0.91 | 2.2 ± 0.6 | 2.2 ± 0.8 |
| | Baseline $FEV_1$ (% pred.) | 64.2 ± 16.7 | 76.1 ± 19.8 | 71.7 ± 19.4 |
| | Baseline FVC (I) | 3.41 ± 1 | 3.1 ± 0.74 | 3.2 ± 0.8 |
| | Baseline FVC (% pred.) | 79.7 ± 13.3 | 87.2 ± 18.3 | 84.5 ± 16.9 |
| | MaxFEV$_1$ Reversal | 24.2 ± 20.7 | 14.7 ± 16 | 18.2 ± 18.2 |
| All Subjects(n = 84) | | 30 (36%) | 54 (64%) | 84 (100%) |
| | Age of onset | 10.9 ± 11.2 | 17.5 ± 13.5 | 15.1 ± 13 |
| | Baseline $FEV_1$ (I) | 3 ± 1.2 | 2.5 ± 0.6 | 2.7 ± 0.9 |
| | Baseline $FEV_1$ (% pred.) | 74.8 ± 20.2 | 83.4 ± 19.2 | 80.3 ± 19.9 |
| | Baseline FVC (I) | 4.3 ± 1.36 | 3.4 ± 0.8 | 3.7 ± 1.1 |
| | Baseline FVC (% pred.) | 88.7 ± 15.5 | 93.4 ± 17.9 | 91.7 ± 17.2 |
| | MaxFEV$_1$ Reversal | 17 ± 17 | 14 ± 14 | 15 ± 15 |

For each sample, 50 mL of bronchoalveolar lavage was clarified by high speed centrifugation (10,000 g for 3 min. at 4° C.). The supernatants were then analyzed for 25 human cytokines (BioSource 25-Plex panel). Duplicate samples and serial dilutions of the cytokine standards (50 mL) were incubated with anti human cytokine coated-beads in 96-well filtration plate (Millipore) for 30 min. In this assay, panels of colored microspheres conjugated with capture antibodies are bound to the sample (each capture antibody is conjugated with a uniquely colored microsphere). This panel includes IL-1b, IL-1Ra, IL-2, IL-2R, IL-4, IL-5, IL-6, IL-7, IL-8, IL-10, IL-12p40, IL-13, IL-15, IL-17, TNF-a, IFN-a, IFN-g, GM-CSF, MIP-1a, MIP-1b, IP-10, MIG, Eotaxin, RANTES, and MCP-1. The plates were vacuum-washed 3 times with 100 mL of wash buffer and incubated with 25 mL of biotinylated antibody cocktail for 30 min. The immune reaction is then be developed by adding 50 mL of streptavidin-phycoerythrin for 10 min followed by 3 washes. The samples are then resuspended in 100 mL of assay buffer and 100 beads of each cytokine are acquired and analyzed. For each cytokine, a standard curve is generated using recombinant proteins to estimate protein concentration in the unknown sample. These assays have a sensitivity comparable to ELISA measurements, with a detection limit of 10-30 ng/L (depending on cytokine), low inter-assay variation (<10%), and with a dynamic range of up to 3 orders of magnitude.

EXAMPLE 3

Data Analysis

Chemokine concentrations were determined based on a simultaneously measured standard curve using a logistic curve-fitting algorithm (Bio-Plex Manager 3.0 Software). The standard curve for each cytokine in this panel has a range between 2 to 5000 pg/ml. Sample data were used when duplicate measurements showed less than 10% difference.

EXAMPLE 4

Hierarchical Clustering

The data were reduced from 25 to 18 features by removing those cytokines for which more than 50% of the data were undetectable. These cytokines were IL-1b, IL-7, IL-10, IL-12, IL-13, IFN-a and GM-CSF. Unsupervised agglomerative ("bottoms up") hierarchical clustering was performed on the 50 percentile normalized data using the unweighted paired group mean (UPGMA) using correlation as the similarity measure (Spotfire Decision Site 9.0). Cytokine values below the level of assay detection were replaced by values representing one tenth the lowest value measured on the standard curve.

EXAMPLE 5

Classifiers and Attribute Reduction

A C4.5 classifier[12] was applied on the 50 percentile normalized cytokine values using entropy for splitting and 10-fold cross validation (WEKA 3.5.3).

EXAMPLE 6

Statistical Analysis

ANOVA with multiple comparisons and Kruskall-Wallis tests were performed using SAS, version 9.1 (SAS, Inc., Cary, N.C.) and SPSS, Release 11.0.1 (SPSS, Inc., Chicago, Ill.). Shrunken centroid classification and feature reduction was performed using prediction analysis in microarray (PAM)[13].

EXAMPLE 7

Results

The subjects studied were 41 "severe" and 43 age and gender matched "non-severe" asthmatics enrolled by the SARP program whose characteristics are shown in Table I. There were no differences in the age of onset or gender distribution between the two groups, with approximately twice as many women as men. Non-severe asthmatics had nearly normal $FEV_1$ (89% predicted) and FVC (99% predicted). Severe asthmatics had significant reductions $FEV_1$ compared to nonsevere (72% vs 89%, p<0.01) and a greater maximal $FEV_1$ reversal after albuterol inhalation (18% vs 12%, p<0.05). These characteristics of female gender enrichment and pulmonary function are representative of severe asthmatic population identified by the SARP criteria (Moore et al., 2007).

The present invention initially focused on molecular profiling on the basis of cytokine measurements because these molecules mediate airway inflammation by recruiting leukocyte populations, affecting $T_H1/T_H2$ balance, and promoting smooth muscle cell proliferation. the expression of 18 cytokines in were detected bronchoalveolar lavage (7 cytokine measurements were not detectable in the majority of subjects and were excluded) and were further analyzed.

EXAMPLE 8

Identification of 4 Asthma Phenotypes

To reveal underlying structure in the data, it was subjected to unsupervised agglomerative hierarchical clustering (FIG. 1). Briefly, this method groups subjects based on mathematical similarities of the bronchoalveolar lavage cytokine concentrations (Eisen et al., 1998). Initially, each subject is in its own cluster. At each step, the nearest two subjects (determined by Pearson's correlation as the distance metric) are combined into a higher-level cluster. The iteration continues until all the subjects are grouped. Each row corresponds to a subject, and the individual cytokine values are shown in each column, with green being low expressing, red being high. From this analysis, four groups (G) labeled G1-G4 could be discerned displaying different patterns of cytokine expression. For example, G1 had high levels of IL-2, G2 had high levels of IL-1Ra, G3 had high levels of IP-10, and G4 had high levels of IL-2R and many other cytokines (FIG. 1).

To determine whether the subjects within these groups represented biologically distinct subgroups of asthma, the clinical features of the four groups were compared with one another. It was found that over 15 different variables were statistically different between these groups (Table II). Importantly, these included cellular features of bronchoalveolar lavage (pulmonary eosinophils, alveolar macrophages) and lung function measurements (values of lung function, $FEV_1$ response to bronchodilation and sensitivity to metacholine).

TABLE II

| Between group differences in G1, 2, 3 and 4 | | |
|---|---|---|
| Function | Characteristic | P-Value (ANOVA) |
| General | BMI | 0.02 |
| BAL Cellularity | Macrophages | 0.05 |

TABLE II-continued

Between group differences in G1, 2, 3 and 4

| Function | Characteristic | P-Value (ANOVA) |
|---|---|---|
| | Lymphocytes | 0.05 |
| | Eosinophils | 0.05 |
| Lung Function (Baseline) | $FEV_1$ | <0.001 |
| | FEV1pp | 0.02 |
| | FVC | <0.001 |
| | FVCpp | 0.03 |
| | Max $FEV_1$/MPV | <0.001 |
| | Max FVC/MPV | <0.001 |
| | Max FVCpp/MPVLung | 0.01 |
| Lung Function (Post Treatment) | logPC20Methacholine | 0.01 |
| | $FEV_1$ Reversal, percent | 0.03 |
| | $FEV_1$ Albuterol reversal | <0.001 |

To further determine how each group differed from one another, pairwise comparisons between the groups was performed using multiple comparisons in ANOVA (with Bonferroni correction). This analysis indicated that the subjects in G1 had a significantly reduced $FEV_1$, FVC, and $FEV_1$ improvement after bronchodilator therapy compared to other groups (Table II).

Moreover, G1 was enriched in subjects classified as "severe" by the ATS criteria (Proceedings of the ATS workshop on refractory Asthma, 2000), with 18 of the 30 subjects (60%) assessed by SARP investigators as having "severe" asthma. G2, the group with the best preservation of lung function was enriched in non-severe asthmatics, with only 8 of the 13 (38%) being identified as "severe" by ATS criteria. These findings indicated that bronchoalveolar lavage cytokine patterns were informative of disease phenotypes as determined by non-overlapping clinical criteria.

EXAMPLE 9

Identification of Cytokines Having Greatest Impact on G1 Classification

Although clustering based on 18 cytokines identified phenotypically distinct subgroups, the cytokines that most contributed to the clustering result were identified. For this purpose, a feature reduction technique using a robust linear discriminant method known as "shrunken centroids" was used. Centroids characterizes each class mathematically as a vector of its means (known as a 'centroid'). Through a re-iterated process of training and cross validation, the number of features were reduced (shrunk) to those with the smallest variation within the class while still retaining classification accuracy. This identified a smaller set of cytokines that were most important in the decision process.

Shrunken centroids were therefore performed to identify minimal features that differentiate subjects in G1 from all the other asthma subtypes combined (G2, G3 and G4). This analysis identified 10 cytokines as being most important for identification of this severe group. The rank order of these cytokines (most informative to least) was IL-1Ra, MIP-1a, MIG, IL-15, IL-2R, IP-10, IL-4, IL-6, MCP-1, and IL-2. Using this group of cytokines the subjects could be accurately clustered into the same groups. Importantly, reducing this panel of discriminant cytokines further to 9 or 8 significantly increased the missclassification error.

EXAMPLE 10

Classification Model for Hyper-Responsiveness to Methacholine

Figure 4:
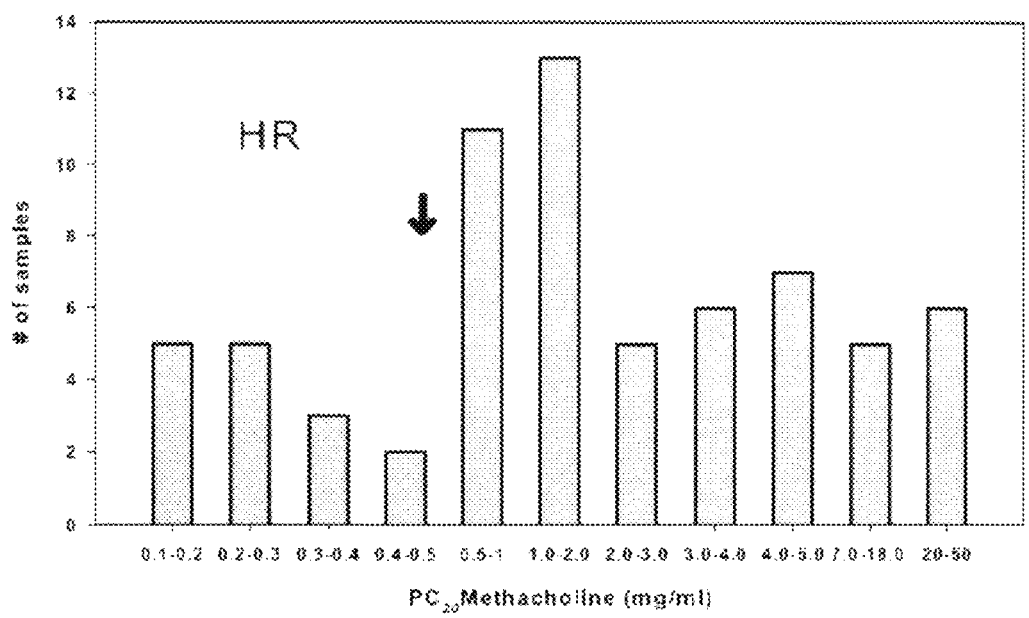
FIG. 4 identifies HR subjects. The figure shows a frequency histogram of the 67 patients where PC20 Methacholine sensitivity was measured. Patients with $PC_{20}$ methacholine response of <0.5 mg/ml were classified as HR.

Cytokine patterns that best predicted airway hyper-responsiveness were identified next. For this purpose "hyper-responders" (HR) were defined using an objective measure, sensitivity to methacholine, a clinical feature identified by the unsupervised analysis (Table II). Of the 84 subjects whose cytokine values were measured, 67 underwent methacholine challenge. Using $PC_{20}$ methacholine as an objective measure of hyper-responsiveness, 15 of the 67 subjects were identified as HR having $PC_{20}$<0.5 mg/ml. A total of 52 subjects were low responders (LR, FIG. 4). Pairwise comparison showed that only one analyte was significantly different between HR and LR (IL-2R, p<0.016, Kruskal-Wallis Test).

Figure 5:
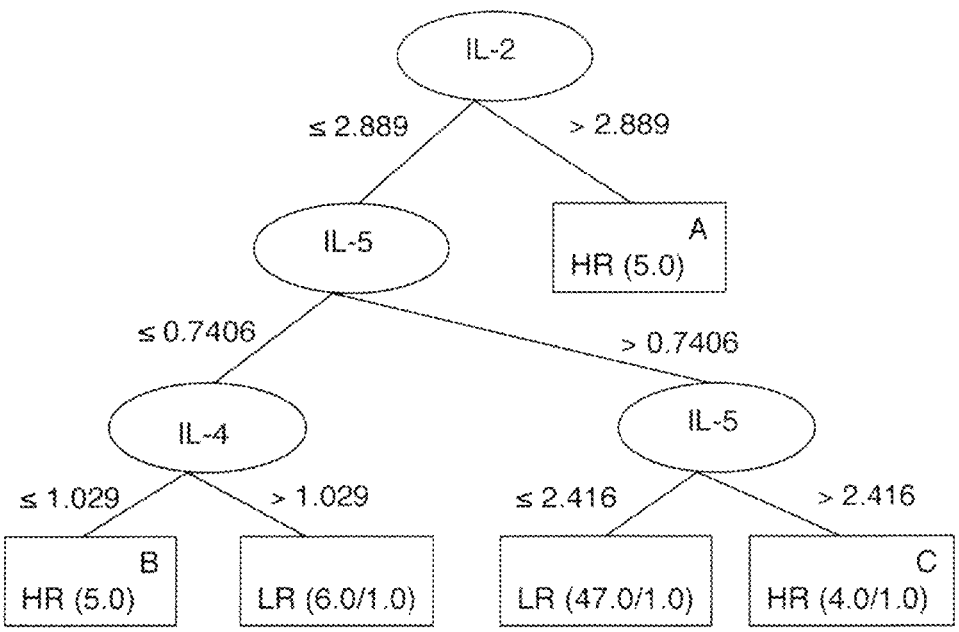
FIG. 5 shows CART classification. C.4.5 decision tree was performed on the Z-Score normalized cytokine data. Shown is the most accurate model. For each node (rectangle) the classification and number of correctly grouped subjects is indicated. The identity of HR classes A, B and C are indicated in upper right hand corner of each terminal leaf.

To determine whether combinations of the cytokines could distinguish HR from LR, the 18 cytokines were subjected to attribute reduction. This process identified IL-2, IL-4, IL-5, TNFa, MIG and RANTES as the most significant attributes. These cytokines were then used in a decision tree based learning method. The cytokine that best separates the HR from the LR is selected first, and the process is repeated. Ten-fold cross validation, a process dividing the data into random training and test sets, is performed to estimate classification error and to prune the tree to prevent over-fitting. Performing 10 trials using 10-fold cross validation resulted in the best model with an average accuracy of 88.1% (FIG. 5). The root node was IL-2 which produced a split identifying 5 HR (Class A). Two more HR classes were identified, with low IL-5 and low IL-4 (Class B), and the other, with high IL-5 (Class C).

Figure 6A:
FIGS. 6A-6B show pair-wise comparison of methacholine HR classes. Demographic variables of methacholine HR Class A, B and C were compared by ANOVA.
Figure 6B:

The clinical demographics were compared for HR Class A, B and C. These groups differed significantly in BAL eosinophils and, interestingly, $PC_{20}$ methacholine (FIGS. 6A-6B). HR Class A had low BAL eosinophils and the lowest $PC_{20}$ methacholine. These results indicated that decision tree separated three distinct HR sub-classes.

Patients

Enrollees in this next study were categorized as "non-severe" or "severe" asthma, on the basis of a standardized manual of procedures (MOP) based on an NHLBI workshop (Wenzel and Busse, 2007; Ad hoc Writing Committee on the Assembly on All, 2000). All enrollees had history, physical examination, spirometry, bronchodilator reversibility, allergy skin testing, and methacholine challenge testing. Non-severe asthmatics have lung function that can be normalized using standard doses of inhaled corticosteroids, with or without long-acting beta-agonists or leukotriene modifiers. Severe asthmatics are defined according to ATS consensus for refractory asthma (Wenzel and Busse, 2007). These patients are characterized by abnormal lung function in the face of aggressive standard inhaled steroid therapy and at least one additional control agent. For pulmonary function testing, baseline $FEV_1$ testing required a 4-6 hr withhold of short acting bronchodilators and a 10-12 hr hold for long acting bronchodilators. Hankonsen predicted values (with race correction) were utilized to obtain "percent predicted" values. For dynamic testing, subjects performed spirometry before and after 4 puffs (90 mg/puff) of albuterol. Methacholine sensitivity was measured as previously described; subjects with a $FEV_1$<75% were excluded for safety reasons. All studies were approved by the local institutional review boards and all subjects gave informed consent.

Bronchoalveolar Lavage (BAL) and Analysis

Bronchoscopy and BAL from 84 randomly selected patients matched for age and gender was performed according to the SARP MOP where infusion of 50 ml of PBS was performed. BAL cellular differential was measured by cytospin preparation cells subsequently stained with H&E. Greater than ≧300 cells were counted for differential analysis. Total cell neutrophil and eosinophils were determined by the product of the differential times the total cell count. For cytokine measurement, clarified BAL was frozen, and analyzed for 25 human cytokines in duplicate (BioSource 25-Plex panel). This panel included included IL-1β, IL-1Ra, IL-2, IL-2R, IL-4, IL-5, IL-6, IL-7, IL-8, IL-10, IL-12p40, IL-13, IL-15, IL-17, TNF-α, IFN-α, IFN-γ, GM-CSF, MIP-1α, MIP-1β, IP-10, MIG, Eotaxin, RANTES, and MCP-1. For each cytokine, a standard curve is generated using recombinant proteins to estimate protein concentration in the unknown sample. Assay sensitivity is a detection limit of 10-30 ng/L (depending on cytokine), low inter-assay variation (<10%), and with a dynamic range of up to 3 orders of magnitude.

Data Analysis

Chemokine concentrations were determined based on a simultaneously measured standard curve using a logistic curve-fitting algorithm (Bio-Plex Manager 3.0 Software). The standard curve for each cytokine in this panel has a range between 2 to 5000 pg/ml. Sample data were used when duplicate measurements showed less than 10% difference. BAL fluid concentrations were analyzed as raw concentrations without normalization to total protein, albumin, or other marker. This strategy is consistent with the recommendation of the Bronchoalveolar Lavage Cooperative Study Group (Bronchoalveolar Lavage Cooperative Steering Committee).

Statistical Analysis

Cytokines whose measurements were undetectable in >50% of subjects were excluded from further analysis. These cytokines were IL-1β, IL-7, IL-10, IL-12p40, IL-13, IFN-β and GM-CSF. ANOVA with multiple comparisons and Kruskall-Wallis tests were performed using SAS, version 9.1.3 (SAS, Inc., Cary, N.C.) and SPSS, Release 11.0.1 (SPSS, Inc., Chicago, Ill.). P values were adjusted using the Benjamini and Hochberg's false discovery rate (FDR) method. Logistic regression modeling was performed using the backward elimination and stepwise selection methods (SAS, Version 9.1.3). A confusion matrix was constructed to calculate the accuracy of prediction for each of the models. Regression coefficients of the statistically significant cytokines (alpha=0.05) included in the regression analysis were used in predicting the corresponding clinical outcome. An ROC curve was used to estimate the performance of the models.

Results

To ensure the data set contained a wide spectrum of clinical phenotypes, study volunteers included 41 "severe" and 43 age and gender matched "non-severe" asthmatics. Relative to non-severe asthmatics, severe asthmatics had significant reductions in $FEV_1$, and a greater maximal $FEV_1$ reversal after albuterol inhalation. These differences in pulmonary function are representative of the severe asthmatic population (Moore et al., 2007).

In this analysis, which objective phenotypes were associated with BAL cytokine patterns was determined. The distribution of BAL cellular components, including absolute eosinophil- and neutrophil counts was examined because BAL eosinophils correlate with clinical severity of asthma (Bousquet et al., 1990), and neutrophilic inflammation has been described in fatal- and severe asthma (Wentzel et al., 1999). The forced expiratory volume in one second ($FEV_1$) response to bronchodilation was measured because $FEV_1$ response may be linked to responsiveness to glucocorticoids (Kerstjens et al., 1993). Finally, methacholine sensitivity was measured, because this is an independent index of airway responsiveness and gives information of independent of bronchodilatory response.

Figure 7A:
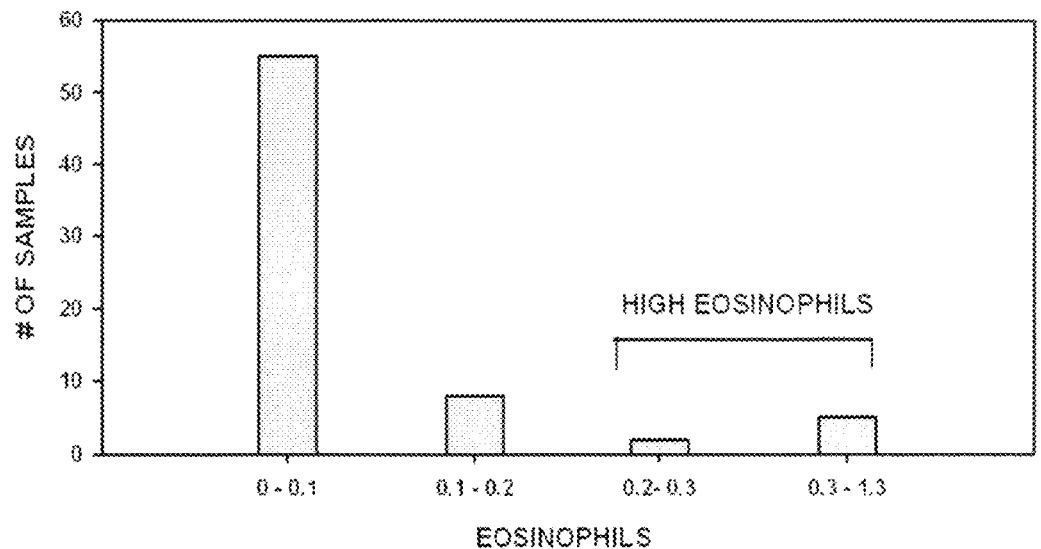
FIGS. 7A-7D show class distributions and definitions. Shown are population histograms of the asthma phenotypes selected for modeling.
Figure 7B:
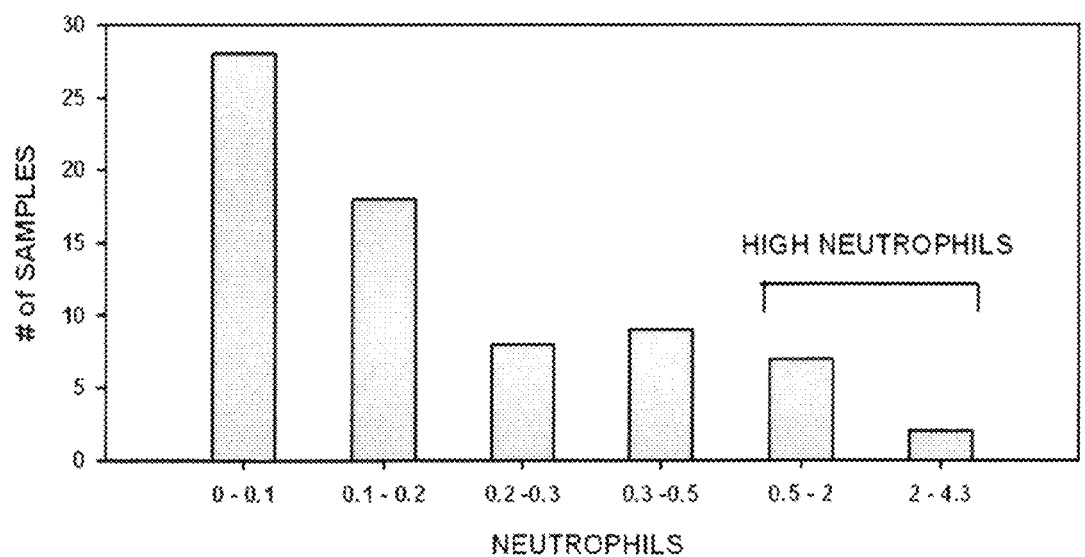
Figure 7C:
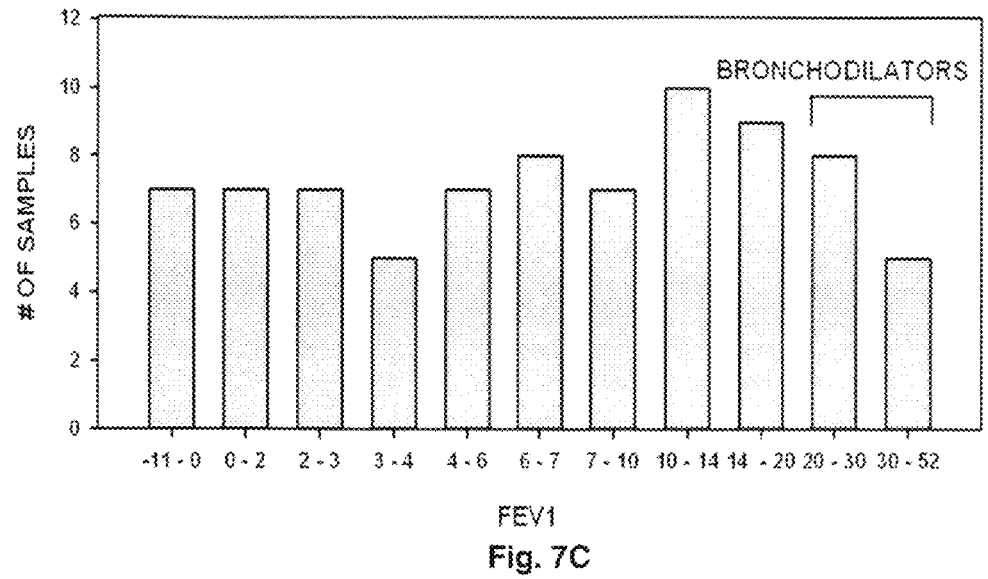
Figure 7D:
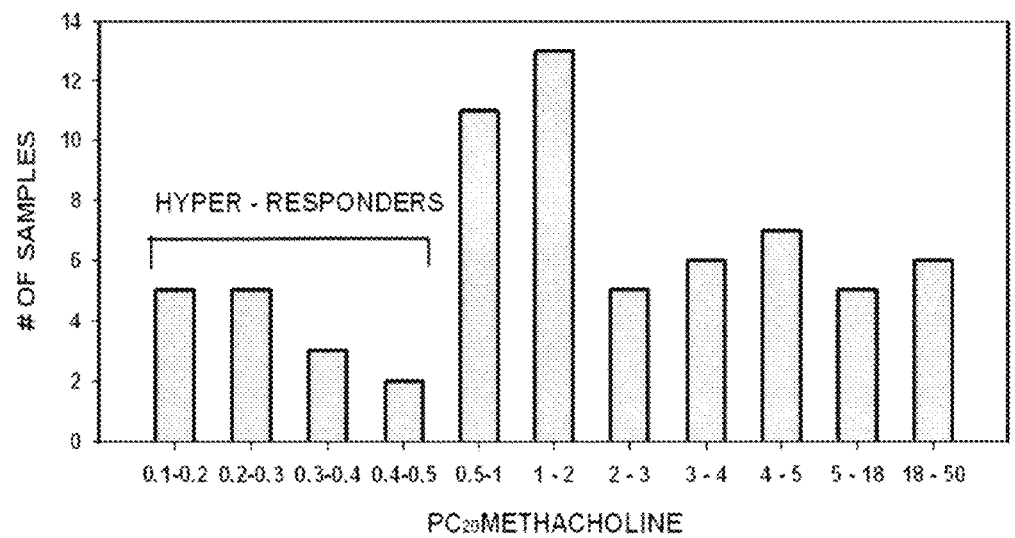

Population histograms were plotted for each phenotype to determine subclasses that represent the most extreme outliers in the subject groups (FIGS. 7A-7D). Eosinophil numbers were distributed in a non-gaussian distribution, with most BALs being clustered around 0 (FIG. 7A). Using an absolute eosinophil count of greater than $0.2 \times 10^6$ eosinophils in the BAL sample, 13 of 72 patients (18%) were designated as the "high eosinophil" class. For neutrophils, the majority of subjects had no neutrophils; using a cut-off of greater than $0.2 \times 10^6$ neutrophils/BAL, 5 of 72 patients (7%) were identified as the high "neutrophil" class. The study population $FEV_1$ response to albuterol was distributed in an apparently Gaussian distribution, where the majority of bronchodilator responses showed an improvement of 0-20% change in percent corrected $FEV_1$; 13 of 83 (15%) had responses of greater than 20% of their baseline $FEV_1$; these patients were identified as "bronchodilators". Finally, a wide distribution of sensitivity to methacholine was identified in the population; $PC_{20}$ values of <0.5 mg/ml were used to identify the "hyper-responder" class, representing 15 of 67 (22%) patients who had methacholine responses measured (note that not all patients had methacholine responses measured as this test was not performed in patients with reduced $FEV_1$; as a result fewer measurements were available for the severe asthmatic group).

Because these phenotypes may be highly correlated, the relative class distribution of the asthmatic phenotypes in the severe and non-severe groups was next examined using set analysis. Members of the high eosinophil group were evenly distributed between non-severe and severe groups, whereas the class representing high neutrophils were uniquely and surprisingly distributed in the non-severe asthmatics. Conversely the bronchodilators were enriched in the severe group; consistent with comparison of the severe vs non-severe asthmatics where the severe asthmatics as a group had a lower $FEV_1$ but a greater bronchodilatory response. The methacholine hyper-responders were evenly distributed in both asthma groups.

Next, the study population membership in all phenotypes were analyzed. The composition of these groups were distinct, with no subject being contained in all groups. The most overlap was 3 subjects being shared between hyper-responders and bronchodilators, representing a minority of the population for either class. Based on this analysis, it was concluded that these cellular and physiological phenotypes are composed of relatively distinct asthma phenotypes.

Logistic Modeling and Analysis

Next, descriptive statistics was applied and predictive models using BAL cytokines were developed and evaluated to identify these four distinct asthmatic phenotypes. For this latter purpose, logistic regression with backward selection was used.

High Eosinophils

Figure 8A:
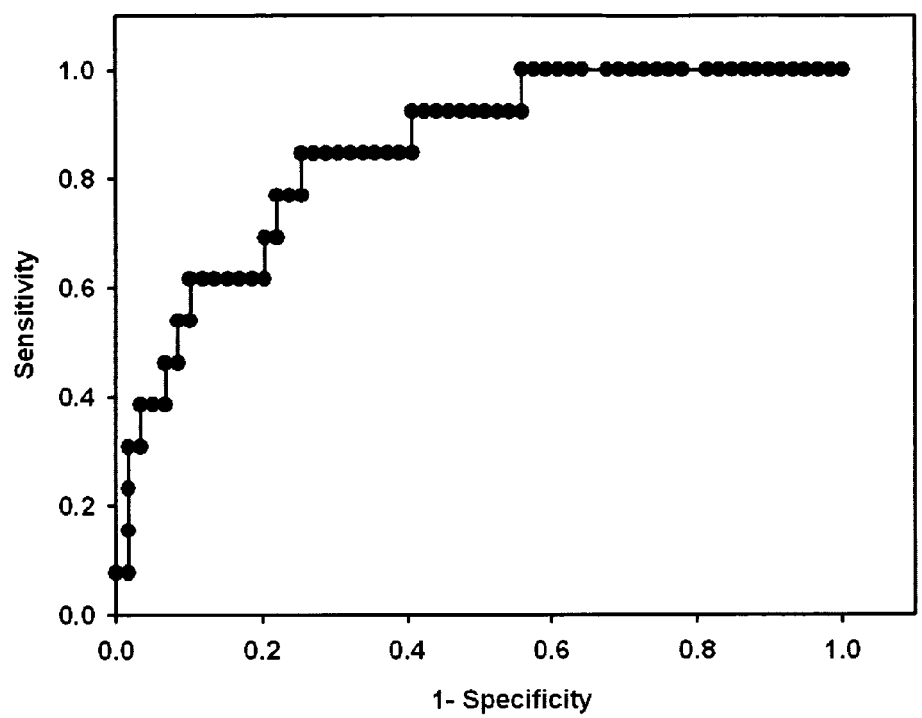
FIGS. 8A-8D show Receiver Operating Curve (ROC).

After nonparametric ANOVA and adjustment for multiple hypothesis testing, no single cytokine was different between the "high eosinophil" and the remaining group. Using logistic regression with backward selection strategy, we identified a model that was 85% accurate for predicting "high eosinophil" using the cytokine values for MIG, Eotaxin, IL-8 and IL-17 (Table III). Using this model, a receiver operator curve (ROC) analysis was performed; this identified with an area under the curve (AUC) of 0.84, indicating a very good model performance (FIG. 8A). For each variable remaining, shown is the odds ratio (OR), 95% confidence interval (95% CI), and p value.

TABLE III

|  | Cytokine | OR | 95% CI | pValue |
|---|---|---|---|---|
| High | MIG | 0.832 | 0.72-0.95 | 0.0078 |
|  | Eotaxin | 0.296 | 0.13-0.65 | 0.0028 |
|  | IL-8 | 1.245 | 1.02-1.5 | 0.0243 |
|  | IL-17 | 1.321 | 1.07-1.61 | 0.0074 |

Neutrophils

Figure 8B:
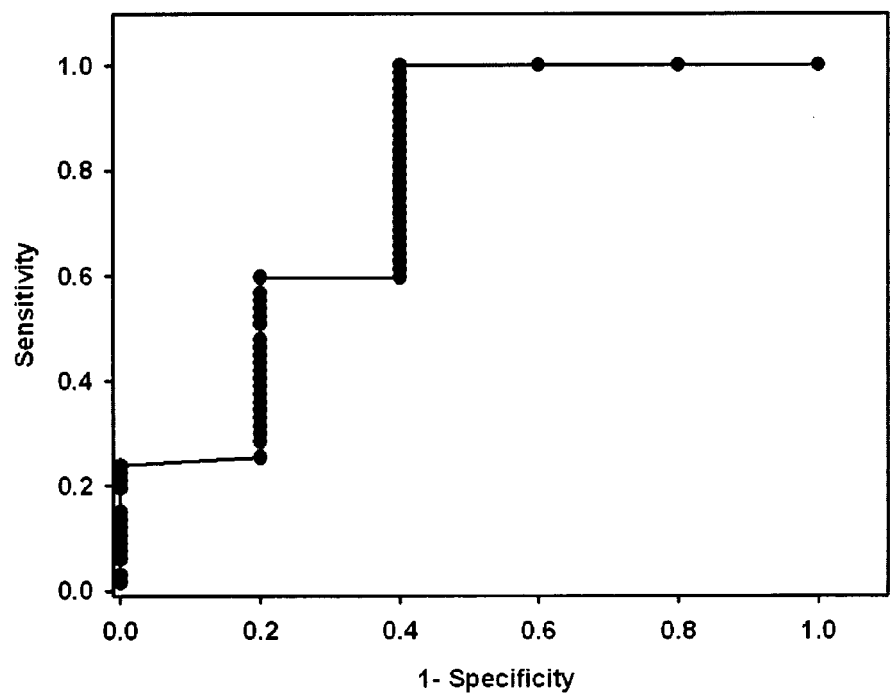

Logistic regression for the "high neutrophil" group, the cytokines IL-15 and IL-6 survived selection, producing a model that was 97% accurate (Table IV). The ROC analysis indicated an AUC of 0.76 (FIG. 8B)

TABLE IV

| Cytokine | OR | 95% CI | pValue |
|---|---|---|---|
| IL-15 | 0.863 | 0.74-1 | 0.0493 |
| IL-6 | 1.270 | 1.07-1.5 | 0.0053 |

Bronchodilators

Figure 8C:
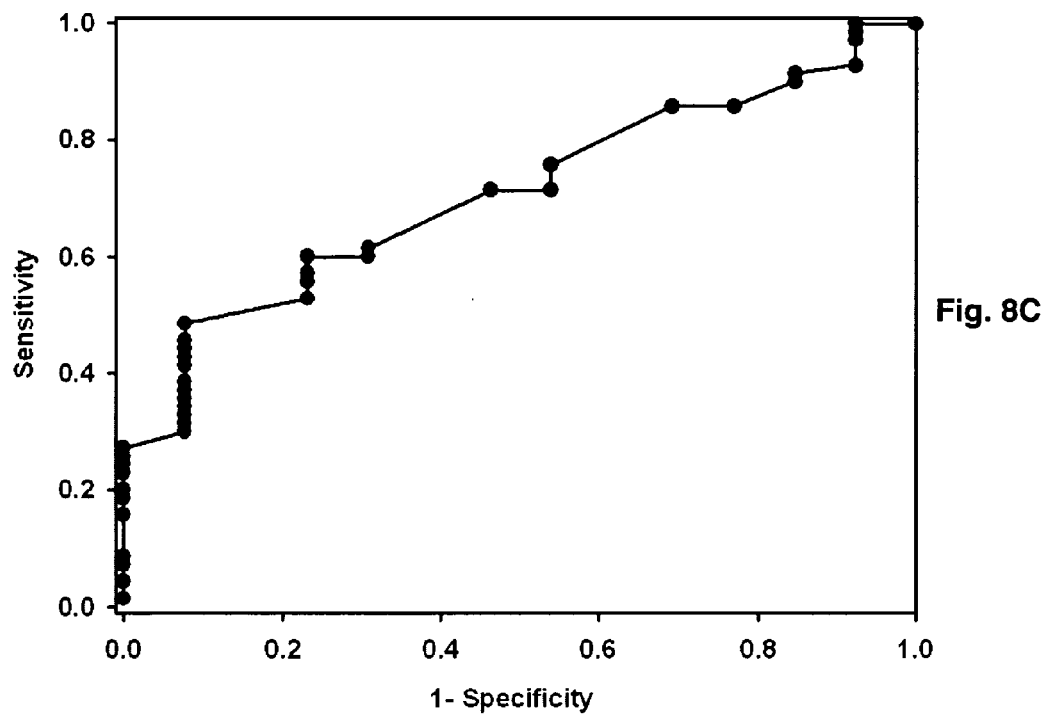

For bronchodilators, only the Eotaxin cytokine survived selection, producing a model that was 86% accurate (Table V) and an AUC of the ROC curve of 0.71 (FIG. 8C).

TABLE V

| Cytokine | OR | 95% CI | pValue |
|---|---|---|---|
| Eotaxin | 2.036 | 1.10-3.75 | 0.0228 |

Methacholine Hyper-Responders

Figure 8D:
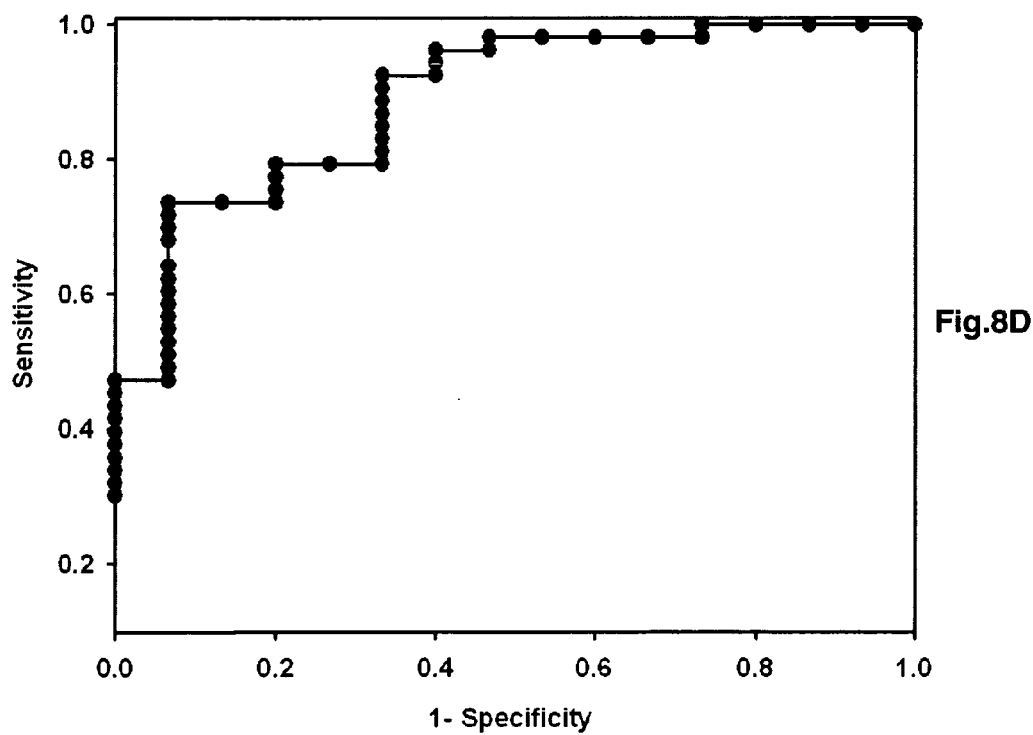

Using nonparametric analysis and correction for multiple hypothesis testing, we found that IL-1Ra was significantly different between methacholine hyper-responders and the remaining subjects (p<0.001, FDR). In logistic regression, 4 cytokines (IL-1Ra, Eotaxin, IL-4 and IL-2R) survived selection, producing a model that was 85% accurate (Table VI) with an AUC of 0.85 (FIG. 8D).

TABLE VI

| Cytokine | OR | 95% CI | pValue |
|---|---|---|---|
| IL-1Ra | 0.983 | 0.97-0.99 | 0.0026 |
| Eotaxin | 8.109 | 1.21-53.96 | 0.0304 |
| IL-4 | 0.522 | 0.30-0.90 | 0.0193 |
| IL-2R | 1.057 | 1.00-1.11 | 0.0441 |

The present invention defined asthmatic subtypes as those that show extremes of objective, quantitative measures. At least 4 phenotypes were associated with distinct BAL cytokine patterns. $FEV_1$ was modeled suggesting that reduction in $FEV_1$ may not be the direct consequence of active mucosal inflammation, or because abnormal FEV1 is part of the definition of severe asthma, the logistic modeling may be unable to differentiate the effect due to confounding factors such as steroid therapy.

In the process of mucosal inflammation characteristic of asthma, local $Th_2$ lymphocytes, eosinophils and mast cells play a role in coordinating the clinical manifestations of disease. The presence of pulmonary eosinophils have been established to correlate with clinical severity of asthma, and are predictive of the response to pharmacological therapy. The processes underlying tissue targeting, and activation of circulating eosinophils are known to be regulated by multiple cytokines, including GM-CSF, IL-5 and IL-3 cytokines, cytokines which also induce tissue survival by persistent signals mediated through a novel cross-talk signaling pathway involving ICAM-1, an adhesion molecule associated with tissue persistence. In this analysis, Eotaxin contributed to the model predicting the subgroup with high BAL eosinophils. Eotaxin is a CC chemokine known to be a potent activator of eosinophil chemotaxis and mediator release via activation of the MAPKs, activated by binding its receptor, CCR3. Eotaxin is highly induced in allergic asthma and in response to segmental airway challenge, where it contributes to eosinophilic recruitment, inflammation and remodeling. In fact, soluble CCR3 inhibitors have shown therapeutic promise for blocking Eotaxin-induced eosinophil activation in the treatment of allergic lung disease. Of the four cytokines selected in this model, Eotaxin contributed the greatest odds ratio (3.375, Table I) to the prediction of the high eosinophil group.

In addition, the modeling of the present invention indicated that IL-17 was negatively correlated with BAL eosinophilia. IL-17 is a member of a cytokine family produced by activated CD4+ memory cells known to promote pulmonary neutrophil emigration. Severe asthmatics have been characterized as having either neutrophil- or eosinophil-predominant inflammation. Consistently, this set analysis indicated that of the 18 subjects with either high neutrophils or high eosinophils, only 1 subject was a member of both classes. These observations suggest that the balance of IL-17/Eotaxin may be important in inducing neutrophil- or eosinophil predominant inflammation.

Neutrophils are a cell type that have been linked to severe asthma, occupational asthma, and childhood asthma. In severe asthma, neutrophils have been identified in sputum, BAL and transbronchial biopsies of small airways. The logistic regression analysis indicated that the cytokine IL-15 positively related, while IL-6 levels were negatively related to the probability of high BAL neutrophils. IL-15 levels were found to be the best predictors of high neutrophils in this analysis. IL-15 is a potent inducer of CXC-type chemokines, known to have chemotactic and activating effects on neutrophils.

A surprising finding of the present invention was that specific BAL cytokines were related to indices of dynamic lung function. There has been interest in assessing bronchodilator response in asthma since the finding that this parameter is associated with improvement in $FEV_1$ in response to chronic glucocorticoid treatment. Although β-adrenergic receptor polymorphisms have been shown to affect response in vitro, these polymorphisms appear not to influence responsiveness to acute bronchodilator response clinically. Interestingly, Eotaxin was the only cytokine that survived the feature selection. It is important to note that group membership for high eosinophils and bronchodilators had little overlap, and Eotaxin is negatively correlated with bronchodilator group, whereas its level is positively correlated with the high eosinophil group.

CART decision trees showed that sequential splits using IL-2, IL-4 and IL-5 could accurately classify hyper-responders with an overall 88% accuracy in 10-fold cross-validation. Logistic regression produced a slightly higher accuracy with an excellent AUC based on IL-1Ra, Eotaxin, IL-4 and IL-2R. Interestingly, all of these cytokines were identified as important variables in the CART decision tree. Consistently, IL-1Ra and Eotaxin were identified by descriptive statistics as being significantly different in the pairwise comparison between hyper-responders and the remainder of the subjects.

The following references were cited herein:

Ad-hoc writing committee of the Assembly on Allergy All. Proceedings of the ATS Workshop on Refractory Asthma. Current Understanding, Recommendations, and Unanswered Questions. American Journal of Respiratory & Critical Care Medicine 2000; 162:2341-51.

Bhattacharjee et al., Proc Natl Acad Sci 2001; 98:13790-5.

Bousquet et al., The New England Journal of Medicine 1990; 323(15):1033-39.

Bronchoalveolar Lavage Cooperative Steering committee. BAL Constituents in Healthy Individuals, Idiopathic Pulmonary Fibrosis and Selected Comparison Groups. Am Rev Respir Dis 1990; 141:S169-S202.

Busse W W and Lemanske R F, N Engl J Med 2001; 344:350-62.

Deykin A., Journal of Allergy and Clinical Immunology 2006; 118(3):565-8.

Eisen M B et al., Proc Natl Acad Sci 1998; 95:14863-8.

Fahy J V et al., Journal of Allergy and Clinical Immunology 1995; 95(4):843-52.

Golub et al., Science 1999; 286(5439):531-7.

Godard P et al., Eur Respir J 2002; 19:61-7.

Holgate et al., Am J Respir Crit Care Med 1997; 156:1377-83.

Jatakanon A N, et al., Am J Respir Crit Care Med 1999; 160(5):1532-9.

Kapp et al., BMC Genomics 2006; 7(1):231.

Kerstjens et al., Eur Respir J 1993; 6(6):868-76.

Lemiere C, et al. Journal Allergy and Clinical Immunology 2006; 118:1033-9.

Leung D Y et al., J Exp Med 1995; 181(1):33-40.

Leung D Y M and Szefler S J., Clinics in Chest Medicine 1997; 18:611-25.

Moore et al. Journal of Allergy and Clinical Immunology 2007; 119(2):405-13.

Moore and Peters, Journal of Allergy & Clinical Immunology 2006; 117:487-94.

Quinlan J R. C4.5: Programs for Machine Learning. Morgan Kauffman, 1993.

Serra-Battles J et al., Eur Respir J 1998; 12:1322-6.

Sousa et al., Thorax 1997; 52(5):407-10.

Thomas M S et al., The Journal of Immunology 2004; 173(1):615-23.Tibshirani et al., Proc of the Nat. Academy of Sciences 2002; 99(10):6567-72.

Wenzel et al. Am J Respir Crit Care Med 1999; 160(3):1001-8.

Wenzel S. Paediatric Respiratory Reviews 2003; 4(4):306-11.

Wenzel and Busse, Jour of Allergy and Clin. Immunology 2007; 119(1):14-21.

Any patents or publications mentioned in this specification are indicative of the levels of those skilled in the art to which the invention pertains. These patents and publications are herein incorporated by reference to the same extent as if it was indicated that each publication was incorporated specifically and individually by reference.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

What is claimed is:

1. A method of differentiating severe asthma from non-severe asthma in an individual, comprising:
    obtaining a respiratory fluid sample from the individual;
    determining the expression of cytokines comprising IL-1Ra, MIP-1a, MIG, IL-15, IL-2R, IP-10, IL-4, IL-6, MCP-1, and IL-2 at the protein level in the sample by means of ELISA; and
    performing statistical analysis to compare the expression level of each cytokine with corresponding expression level of said cytokine in reference sample obtained from a reference non-severe asthmatic population, wherein statistically significant reduced expression levels of IL-1Ra, MIP-1a, MIG, IL-15, IL-2R, IP-10, IL-6, MCP-1, and statistically significant increased expression levels of IL-4 and IL-2 in the sample from the individual compared to the corresponding expression levels in the reference sample indicates that the individual has severe asthma.

2. The method of claim 1, wherein the statistical analysis is hierarchical cluster analysis.

3. The method of claim 1, wherein the individual is an individual at risk or suspected of suffering from asthma or previously diagnosed with asthma.

4. The method of claim 1, wherein the individual classified to have a specific subgroup of asthma is used to select the type and duration of anti-asthma treatment, wherein the classification of subgroups of asthma is based on the expression levels of cytokines recited in claim 1, wherein the subgroups are severe asthma and non-severe asthma, wherein individual classified to have severe asthma can receive a more intense treatment than an individual classified to have non-severe asthma.

* * * * *